US012685516B2

(12) United States Patent
Poland et al.

(10) Patent No.: US 12,685,516 B2
(45) Date of Patent: Jul. 21, 2026

(54) ULTRASOUND IMAGING

(71) Applicant: KONINKLIJKE PHILIPS N.V.,
Eindhoven (NL)

(72) Inventors: McKee Dunn Poland, Andover, MA
(US); James Christopher Taylor, State
College, PA (US)

(73) Assignee: KONINKLIJKE PHILIPS N.V.,
Eindhoven (NL)

( * ) Notice: Subject to any disclaimer, the term of this
patent is extended or adjusted under 35
U.S.C. 154(b) by 0 days.

(21) Appl. No.: 18/860,277

(22) PCT Filed: Apr. 23, 2023

(86) PCT No.: PCT/EP2023/060554
§ 371 (c)(1),
(2) Date: Oct. 25, 2024

(87) PCT Pub. No.: WO2023/208790
PCT Pub. Date: Nov. 2, 2023

(65) Prior Publication Data
US 2025/0312016 A1     Oct. 9, 2025

Related U.S. Application Data

(60) Provisional application No. 63/335,807, filed on Apr.
28, 2022.

(30) Foreign Application Priority Data

May 10, 2022     (EP) ..................................... 22172484

(51) Int. Cl.
A61B 8/00              (2006.01)
(52) U.S. Cl.
CPC .............. A61B 8/54 (2013.01); A61B 8/4236
(2013.01); A61B 8/4281 (2013.01); A61B
8/429 (2013.01);
(Continued)

(58) Field of Classification Search
CPC ....... A61B 8/54; A61B 8/4236; A61B 8/4281;
A61B 8/429; A61B 8/4427; A61B
8/4472; A61B 8/467; A61B 8/4488
See application file for complete search history.

(56) References Cited

U.S. PATENT DOCUMENTS 5,997,479 A     12/1999  Savord et al.
6,013,032 A      1/2000  Savord
(Continued)

FOREIGN PATENT DOCUMENTS

CA        2569409 A1   11/2005
WO     2013048912 A1    4/2013
WO     2019030282 A1    2/2019

OTHER PUBLICATIONS

International Search Report and Written Opinion for PCT/EP2023/
060554; Mailing date: Jun. 29, 2023, 10 pages.
(Continued)

*Primary Examiner* — Baisakhi Roy

(57)               ABSTRACT

A mechanism for initiating ultrasound scanning in a way that
reduces power consumption. An actuation mechanism (250)
generates an actuation signal that indicates whether or not
there is an interaction (between the actuation mechanism
and an operator) that increases a force applied by an ultra-
sound probe (210) to a subject (290), e.g., from a baseline
force. Ultrasound scanning is initiated responsive to the
occurrence of such an interaction. In particular, an ultra-
sound processing system (220) initiates ultrasound scanning
of the subject at an initial frame rate, using an ultrasound
acoustic sensor (240) of the ultrasound probe, responsive to
the actuation signal indicating that there is an interaction
between the actuation mechanism and the operator of the
ultrasound probe; obtains ultrasound imaging data are
acquired by the ultrasound acoustic sensor (240) at the initial
frame rate; processes the ultrasound imaging data to deter-
(Continued)

mine a pressure exerted by the ultrasound probe on the subject; and initiates ultrasound scanning of the subject at a desired frame rate responsive to a determination that the pressure exceeds a full scan pressure threshold, wherein the desired frame rate is higher than the initial frame rate.

15 Claims, 3 Drawing Sheets

(52) U.S. Cl.
CPC .......... *A61B 8/4427* (2013.01); *A61B 8/4472* (2013.01); *A61B 8/467* (2013.01); *A61B 8/4488* (2013.01)

(56) References Cited

U.S. PATENT DOCUMENTS

| | | | |
|---|---|---|---|
| 6,283,919 B1 | 9/2001 | Roundhill et al. | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 8,753,278 B2 | 6/2014 | Stoll | |
| 9,456,800 B2 * | 10/2016 | Anthony .............. | A61B 8/4209 |
| 9,504,446 B2 | 11/2016 | Jaeger et al. | |
| 9,808,224 B2 * | 11/2017 | Chen ...................... | A61B 8/403 |
| 2006/0264751 A1 * | 11/2006 | Wendelken .......... | A61B 8/4281 601/1 |
| 2007/0112266 A1 * | 5/2007 | Kishimoto ............... | A61B 8/13 600/463 |
| 2012/0277640 A1 | 11/2012 | Lewis, Jr. et al. | |
| 2015/0265253 A1 | 9/2015 | Kim et al. | |
| 2017/0049331 A1 | 2/2017 | Suzuki | |
| 2017/0303899 A1 * | 10/2017 | Willsie ................... | A61B 8/461 |
| 2019/0069842 A1 | 3/2019 | Rothberg et al. | |
| 2019/0307423 A1 * | 10/2019 | Han ..................... | F16M 13/022 |
| 2019/0321007 A1 | 10/2019 | Hakkens et al. | |
| 2019/0388056 A1 | 12/2019 | Rodriquez | |
| 2020/0029934 A1 | 1/2020 | Sandrin | |
| 2020/0033461 A1 * | 1/2020 | Imai ...................... | A61B 8/546 |
| 2020/0359997 A1 * | 11/2020 | Caswell ............. | A61B 1/00087 |
| 2021/0145414 A1 | 5/2021 | Somerville et al. | |

OTHER PUBLICATIONS

Bilgen, M. et al., "Deformation models and correlation analysis in elastography," J Acoust Soc Am., 1996, vol. 99, Issue 5, Abstract Only.

Pinton, G.F. et al., "Rapid tracking of small displacements with ultrasound," IEEE Transactions on Ultrasonics, Ferroelectrics, and Frequency Control, 2006, vol. 53, No. 6, pp. 1103-1117.

\* cited by examiner

300

1

ULTRASOUND IMAGING

CROSS-REFERENCE TO PRIOR APPLICATIONS

This application is the U.S. National Phase application under 35 U.S.C. § 371 of International Application No. PCT/EP2023/060554, filed on Apr. 23, 2023, which claims the benefit of U.S. Provisional Patent Application No. 63/335,807, filed Apr. 28, 2022, and European Patent Application No. 22172484.2, filed on May 10, 2022. These applications are hereby incorporated by reference herein.

FIELD OF THE INVENTION

The invention relates to the field of ultrasound imaging.

BACKGROUND OF THE INVENTION

US 2019/069842 A1 discloses an ultrasound-on-a-chip device configured to be bound to a user's wrist.

Wearable ultrasound devices (e.g., ultrasound patches) are becoming increasingly popular, particularly for longitudinal monitoring of a subject.

Subjects are generally required to wear wearable ultrasound devices for at least several hours, and sometimes for days. Wearable ultrasound devices therefore need to be small, light and comfortable to a subject to wear. They also need to remain ready for operation for a period of hours or days.

Wearable ultrasound devices also require good acoustic coupling to a subject's body in order to scan effectively. For some ultrasound imaging applications, such as cardiac and lung imaging, the ultrasound device needs to exert significant pressure on the subject to achieve good acoustic coupling. In some cases, it is necessary to push the ultrasound device through layers of surface fatty tissue or between ribs.

Existing approaches for providing this pressure include strapping accessories for classic ultrasound probes, but these are bulky, non-sterile and uncomfortable for a subject. Other mechanisms for providing pressure, such as pneumatic approaches and adhesive spring mechanisms do not provide sufficient pressure for many imaging applications.

SUMMARY OF THE INVENTION

It is an object of the invention to reduce power consumption of an ultrasound sensor.

The invention is defined by the independent claims. The dependent claims define advantageous embodiments.

According to examples in accordance with an aspect of the invention, there is provided an ultrasound device, comprising an ultrasound acoustic sensor, an actuation mechanism, and an ultrasound processing system. The actuation mechanism is configured to generate an actuation signal that indicates whether or not there is an interaction between the actuation mechanism and an operator of the ultrasound device, wherein the interaction increases a force applied by the ultrasound device to a subject. The ultrasound processing system is configured to initiate ultrasound scanning of the subject, using the ultrasound acoustic sensor, responsive to the actuation signal indicating that there is an interaction between the actuation mechanism and the operator of the ultrasound device.

The proposed approach effectively provides a mechanism for automatically activating an ultrasound scan by pressing the ultrasound device against the subject's skin. This pressing may be done manually by an operator of the ultrasound device, for example, by the subject or by a clinician.

The inventors have recognized that, for many ultrasound imaging applications, it is necessary for an ultrasound device to apply force/pressure to the surface of a subject's skin in order to obtain useful imaging data, and that the application of force/pressure could serve an additional purpose of actuating or activating the ultrasound device, i.e., to begin a scan.

Looked at from the opposite perspective, unless an ultrasound device scans continuously, the ultrasound device must be activated in order to start a scan. By using a force/pressure exerted by the device on the subject to activate an ultrasound scan, pressure is applied in the direction in which coupling pressure must be applied. The operation of this actuation mechanism therefore also creates coupling pressure.

In other words, the inventors have recognized that the application of force/pressure in a direction substantially perpendicular to an emitting surface of an ultrasound transducer (i.e., towards the subject) may serve a dual purpose: activating an ultrasound scan and providing the pressure needed to scan effectively.

Any scanning performed while no pressure is applied will not result in useful imaging data, so only scanning when the ultrasound device is pressed against the subject increases a likelihood that imaging data obtained by the ultrasound device can be used for clinical purposes.

The ultrasound device may be dormant (i.e., not emitting/receiving an ultrasound signal) until the application of pressure is detected and a scan is initiated. While the ultrasound device is dormant, it consumes very little power, conserving battery charge of the ultrasound device.

Using an actuation mechanism for the ultrasound device that requires an interaction involving the application of a force/pressure means that, where the ultrasound device is a wearable device, the ultrasound device need not apply any pressure to the subject between ultrasound scans, making the ultrasound device more comfortable to wear without reducing a scan's effectiveness.

The ultrasound processing system of the ultrasound device determines when there is an interaction that increases a force/pressure applied by the ultrasound device to the subject by obtaining, from the actuation mechanism, an actuation signal responsive to such interactions, and processing the actuation signal to determine whether or not there is an interaction between the actuation mechanism and the operator of the ultrasound device.

In some examples, the actuation mechanism comprises a touch sensor located on a surface of the ultrasound device opposite to an ultrasound-emitting surface of the ultrasound acoustic sensor; the actuation signal carries touch data from the touch sensor; and the ultrasound processing system initiates ultrasound scanning of the subject by: processing the touch data to determine whether a user is touching the touch sensor; and initiating ultrasound scanning of the subject responsive to a determination that a user is touching the touch sensor.

In this approach, the presence of a touch indicates the occurrence of an interaction between the actuation mechanism and an operator of the ultrasound device that increases a force applied by the ultrasound device to a subject.

The inventors have recognized that the direction of a touch pressure on the surface of the ultrasound device opposite to the ultrasound-emitting surface would be aligned so as to be congruent with pressure being applied by the device on the subject, as a user touching this surface will push the device towards the subject. In this case, a binary touch/no touch determination suffices to activate an ultrasound scan. The pressure of the touch may be able to create the necessary or sufficient coupling pressure on the opposite side of the ultrasound device. The alignment, by design, of the force required for touch sensor activation and the force required for patient coupling serves the purpose of both actuation and coupling. The benefit is efficiency and simplicity in that both functions are achieved by a single user action.

The touch sensor may, for example, by a capacitive sensor. Other suitable touch sensors are known in the art.

In some examples, the ultrasound processing system is configured to initiate scanning of the subject at an initial frame rate responsive to determining that the user is touching the touch sensor.

The ultrasound processing system is advantageously configured to: obtain ultrasound imaging data acquired by the ultrasound acoustic sensor at an initial frame rate; process the ultrasound imaging data to determine a pressure exerted by the ultrasound device on the subject and initiate ultrasound scanning of the subject at a desired frame rate responsive to a determination that the pressure exceeds a full scan pressure threshold, wherein the desired frame rate is higher than the initial frame rate.

In other words, a determination that a user is touching the ultrasound device initiates an ultrasound scan at a low or initial frame rate, i.e., a frame rate that is lower than a desired frame rate for obtaining clinically useful ultrasound imaging data. This scan can be labelled an initial frame rate scan. The ultrasound imaging data acquired at the initial, low frame rate, is usable to determine the pressure exerted by the ultrasound device. If this pressure is sufficient for effective scanning (i.e., exceeds a full scan pressure threshold), the ultrasound device then begins to scan at a desired frame rate, i.e., begins a full frame rate scan. The desired frame rate is a frame rate suitable for obtaining clinically useful ultrasound imaging data, i.e., is greater than the initial frame rate.

The value of the full scan pressure threshold may depend on the ultrasound imaging application being carried out. For example, cardiac ultrasound imaging requires more pressure than vessel imaging on the neck.

Only scanning at the low frame rate when a user touch is detected, rather than continuously scanning at the low frame rate until the pressure exceeds the full scan pressure threshold, conserves a battery charge of the ultrasound device. The ultrasound device may be dormant (i.e., not emitting/receiving an ultrasound signal) until it is touched by a user.

Scanning at an initial low frame rate from the time at which the ultrasound device is first touched until it is determined that the pressure has exceeded the full scan pressure threshold, rather than scanning at the desired frame rate as soon as the user touches the ultrasound device, also reduces unnecessary power consumption of the ultrasound device, further prolonging its battery charge. A scan at a low frame rate provides sufficient ultrasound imaging data to determine the pressure exerted by the device.

The ultrasound imaging data may be processed to determine a measure of deformation of the subject's skin or of an acoustically translucent standoff positioned between the ultrasound acoustic sensor and the subject's skin (e.g., an aqueous gel pad). The deformation is caused by the ultrasound device exerting pressure on the subject, so the measure of deformation may be used to determine the pressure.

In some examples, the ultrasound processing system is further configured to, in response to a determination that the pressure does not exceed the full scan pressure threshold:

generate an indication that more pressure is required; and control a feedback unit to provide a user-perceptible output representative of the indication that more pressure is required.

In this way, the operator who has touched the ultrasound device in order to activate a scan may be alerted when the ultrasound device is not exerting sufficient pressure on the subject for effective scanning. The inventors have recognized that ultrasound devices, and particularly wearable ultrasound devices, are not always operated by an expert sonographer, and that users with little or no training in sonography may be unsure how much pressure they need to apply.

The touch sensor of the ultrasound device may be located on a non-ultrasound-emitting surface of the ultrasound device. Preferably, the touch sensor region is located on a surface opposite to the ultrasound-emitting surface of the ultrasound device, i.e., opposite the ultrasound acoustic sensor.

In some examples, the ultrasound processing system is further configured to, in response to a determination that the pressure exceeds the full scan pressure threshold: generate an indication that a current pressure is correct; and control the feedback unit to provide a user-perceptible output representative of the indication that the current pressure is correct.

This helps to prevent the user from continuing to increase the pressure exerted by the ultrasound device on the subject once the full scan pressure threshold has been reached. Excessive pressure may cause discomfort, and in some cases damage, to the subject and/or the ultrasound device.

Alternatively, the user may recognize that the correct pressure has been reached because an indication that more pressure is required is no longer being displayed or conveyed in another way to the user, e.g., via tactile perceptive feedback.

In some examples, the processing system is further configured to control the ultrasound device to stop acquiring ultrasound imaging data at the desired frame rate in response to a determination that the pressure no longer exceeds the full scan pressure threshold.

This provides a simple mechanism for ending an ultrasound scan: the scan lasts only as long as the ultrasound device is pressed against the subject.

Alternatively, in some examples in which the processing system is configured to determine whether a desired amount of ultrasound imaging data has been obtained (as described below), the processing system may be configured to control the ultrasound device to stop acquiring ultrasound imaging data at the desired frame rate in response to a determination that the ultrasound device has obtained the desired amount of ultrasound imaging data (e.g., based on scanning time and/or the obtained ultrasound imaging data).

In some examples, the actuation mechanism comprises a pressure sensor, the actuation signal carries pressure data from the pressure sensor; and the ultrasound processing system initiates ultrasound scanning of the subject by: processing the pressure data to determine the pressure exerted by the ultrasound device on the subject; and initiating ultrasound scanning of the subject responsive to a determination that the pressure exceeds an activation pressure threshold.

In this approach, a pressure exceeding an activation pressure threshold indicates the occurrence of an interaction between the actuation mechanism and an operator of the ultrasound device that increases a force applied by the ultrasound device to a subject. In other words, the interaction between the actuation mechanism and the operator of the ultrasound device may be an application of pressure that is detected by the pressure sensor. An ultrasound scan is initiated in response to a determination that the detected pressure exceeds a threshold for effective scanning.

The pressure sensor may be positioned between the ultrasound device and the subject.

In some examples, the ultrasound processing system is further configured to, in response to a determination that the pressure does not exceed the activation pressure threshold but does exceed an interaction pressure threshold, lower than the activation pressure threshold: generate an indication that more pressure is required; and control the feedback unit to provide a user-perceptible output representative of the indication that more pressure is required.

Again, this allows a user who is pressing the ultrasound device but with insufficient pressure to be alerted to the fact that more pressure is required. The use of the interaction pressure threshold prevents the feedback from continuously providing this output between scans when no pressure is applied, since where a pressure sensor is used as the actuation mechanism rather than a touch sensor, a pressure determination is required in order to determine whether a user is trying to activate a scan.

The interaction pressure threshold is a non-negative pressure threshold (i.e., the indication is only generated when some pressure is exerted by the ultrasound device on the subject). Preferably, the interaction pressure threshold is a non-zero pressure threshold, in order to reduce a likelihood of generating an indication in response to noise.

In some examples, the ultrasound processing system is further configured to, in response to a determination that the pressure exceeds the activation pressure threshold: generate an indication that a current pressure is correct; and control the feedback unit to provide a user-perceptible output representative of the indication that the current pressure is correct.

This helps to prevent the user from continuing to increase the pressure exerted by the ultrasound device on the subject once the activation pressure threshold has been reached. Excessive pressure may cause discomfort, and in some cases damage, to the subject and/or the ultrasound device.

Alternatively, the user may recognize that the correct pressure has been reached because an indication that more pressure is required is no longer being displayed or conveyed in another way to the user, e.g., via tactile perceptive feedback.

In some examples, the processing system is further configured to control the ultrasound device to stop acquiring ultrasound imaging data at the desired frame rate in response to a determination that the pressure no longer exceeds the activation pressure threshold.

This provides a simple mechanism for ending an ultrasound scan: the scan lasts only as long as the ultrasound device is pressed against the subject.

Alternatively, in some examples in which the processing system is configured to determine whether a desired amount of ultrasound imaging data has been obtained (as described below), the processing system may be configured to control the ultrasound device to stop acquiring ultrasound imaging data at the desired frame rate in response to a determination that the ultrasound device has obtained the desired amount of ultrasound imaging data (e.g., based on scanning time and/or the obtained ultrasound imaging data).

In some examples, the ultrasound processing system is further configured to: determine whether the ultrasound device has obtained a desired amount of ultrasound imaging data during a current ultrasound scan; generate an indication that scanning is completed in response to a determination that the ultrasound device has obtained the desired amount of ultrasound imaging data; and control the feedback unit to provide a user-perceptible output representative of the indication that scanning is completed. In this way, the user is informed when to stop applying pressure. This allows a user to avoid pressing the ultrasound device against the subject for longer than is necessary for imaging purposes, reducing subject discomfort.

The ultrasound processing system may detect when a desired amount of ultrasound imaging data has been obtained based on scanning time, standard heuristic checks on the obtained ultrasound imaging data and/or the output of one or more machine learning algorithms (e.g., a machine learning algorithm trained to identify anatomical structures in ultrasound imaging data).

In some examples, the ultrasound processing system is further configured to: determine a time since the ultrasound device most recently acquired ultrasound imaging data; and, in response to a determination that the time since the ultrasound device most recently acquired ultrasound imaging data exceeds a predetermined period: generate an indication that it is time to perform a scan; and control the feedback unit to provide a user-perceptible output representative of the indication that it is time to perform a scan.

An indication that a time since a most recent ultrasound scan exceeds a predetermined period may be particularly useful in busy clinical settings (such as intensive care units) and where the scan is activated by the subject (e.g., if the subject is performing the scan at home).

In some examples, the ultrasound device further comprises an adhesive layer for attaching the ultrasound device to the subject.

The use of the application of pressure to activate an ultrasound scan is particularly advantageous if the ultrasound device is a wearable device that is attached to the subject for long periods of time. This activation method makes the ultrasound device more comfortable to wear, since the ultrasound device only applies pressure while it is performing a scan, and not continuously.

In some examples, the ultrasound device further comprises an acoustically translucent standoff on an opposite surface of the adhesive layer to a surface for attaching the ultrasound device to the subject In other words, an acoustically translucent standoff may be positioned between the ultrasound acoustic sensor and the subject during a scan. The acoustically translucent standoff may, for example, be an aqueous gel pad. The acoustically translucent standoff may provide acoustic coupling of the ultrasound device to the subject. Deformation of the acoustically translucent standoff may be measured (based on ultrasound imaging data) in order to determine the pressure exerted by the ultrasound device on the subject.

In some examples, the ultrasound device comprises a feedback unit comprising one or more LEDs positioned at or near a perimeter of the ultrasound device and controllable by the processing system.

The one or more LEDs may be used to indicate that scanning is completed, that more pressure is required, that the current pressure is correct and/or that it is time to perform a scan. The one or more LEDs may be RGB LEDs, and different colors may be used for different indications, or different LEDs may be used for different indications.

Positioning the one or more LEDs at or near a perimeter of the ultrasound device allows the light emitted by the one or more LEDs to be seen while a user is pressing the ultrasound device against the subject.

The ultrasound device may comprise other types of feedback unit (e.g., a speaker, a motor to induce vibration, etc.). Feedback may be provided via a separate feedback unit (i.e., separate to the ultrasound device), such as a display device. Feedback may be transmitted wirelessly to a remote device such as a tablet or phone.

According to another aspect of the invention, there is provided a computer-implemented method for performing an ultrasound scan on a subject. The computer-implemented method comprises: obtaining an actuation signal generated by an actuation mechanism of an ultrasound probe, wherein the actuation signal indicates whether or not there is an interaction between the actuation mechanism and an operator of the ultrasound device, wherein the interaction increases a force applied by the ultrasound probe to a subject; and initiating ultrasound scanning of the subject, using an ultrasound acoustic sensor of the ultrasound probe, responsive to the actuation signal indicating that there is an interaction between the actuation mechanism and the operator of the ultrasound probe.

There is also proposed a computer program product comprising computer program code which, when executed on a computer device having a processing system, causes the processing system to perform a method described herein.

Yet another aspect of the invention provides an ultrasound processing system configured to perform a method described herein.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
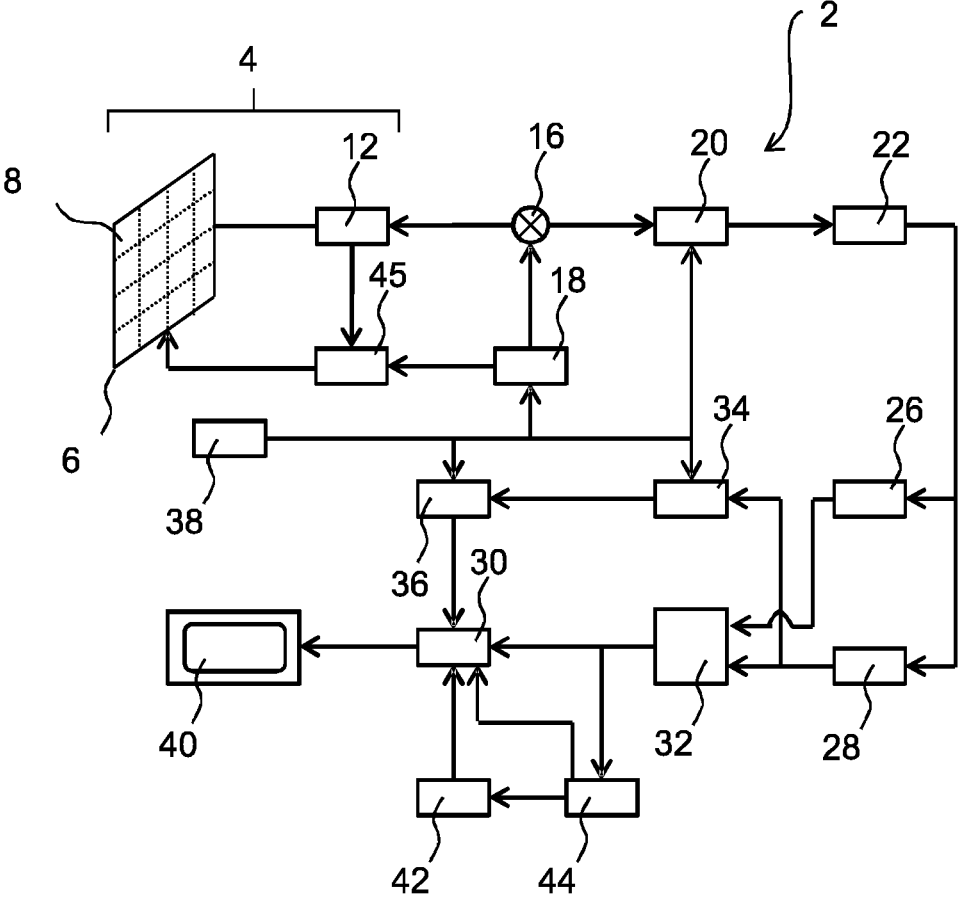
FIG. 1 illustrates an exemplary ultrasound system.

The invention will now be described with reference to the Figures. It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

There is proposed a mechanism for initiating ultrasound scanning using an ultrasound device and a corresponding ultrasound device. An actuation mechanism generates an actuation signal that indicates whether or not there is an interaction (between the actuation mechanism and an operator) that increases a force applied by the ultrasound device to the subject (e.g., from a baseline force). Ultrasound scanning is initiated responsive to the occurrence of such an interaction.

Embodiments are at least partly based on the realization that an application of force or pressure in a scanning direction of the ultrasound device may be used both to activate an ultrasound scan and to provide sufficient acoustic coupling to the subject to produce clinically useful imaging data. Illustrative embodiments may, for example, be employed in ultrasound imaging systems, such as point-of-care ultrasound systems.

In the context of the present disclosure, the terms "user" and "operator" are considered interchangeable.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three-dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one-dimensional line of transducers or a two-dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above-described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g., the harmonics of the main harmonic).

The RF signals may then be coupled to a B mode (i.e., brightness mode, or so-called "2D" imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical or spherical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two-dimensional (2D) sector-shaped format, or a pyramidal three-dimensional (3D) image. The scan converter can overlay a B mode structural image with colors corresponding to motion at points in the image field, where the Doppler-estimated velocities to produce a given color. The combined B-mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
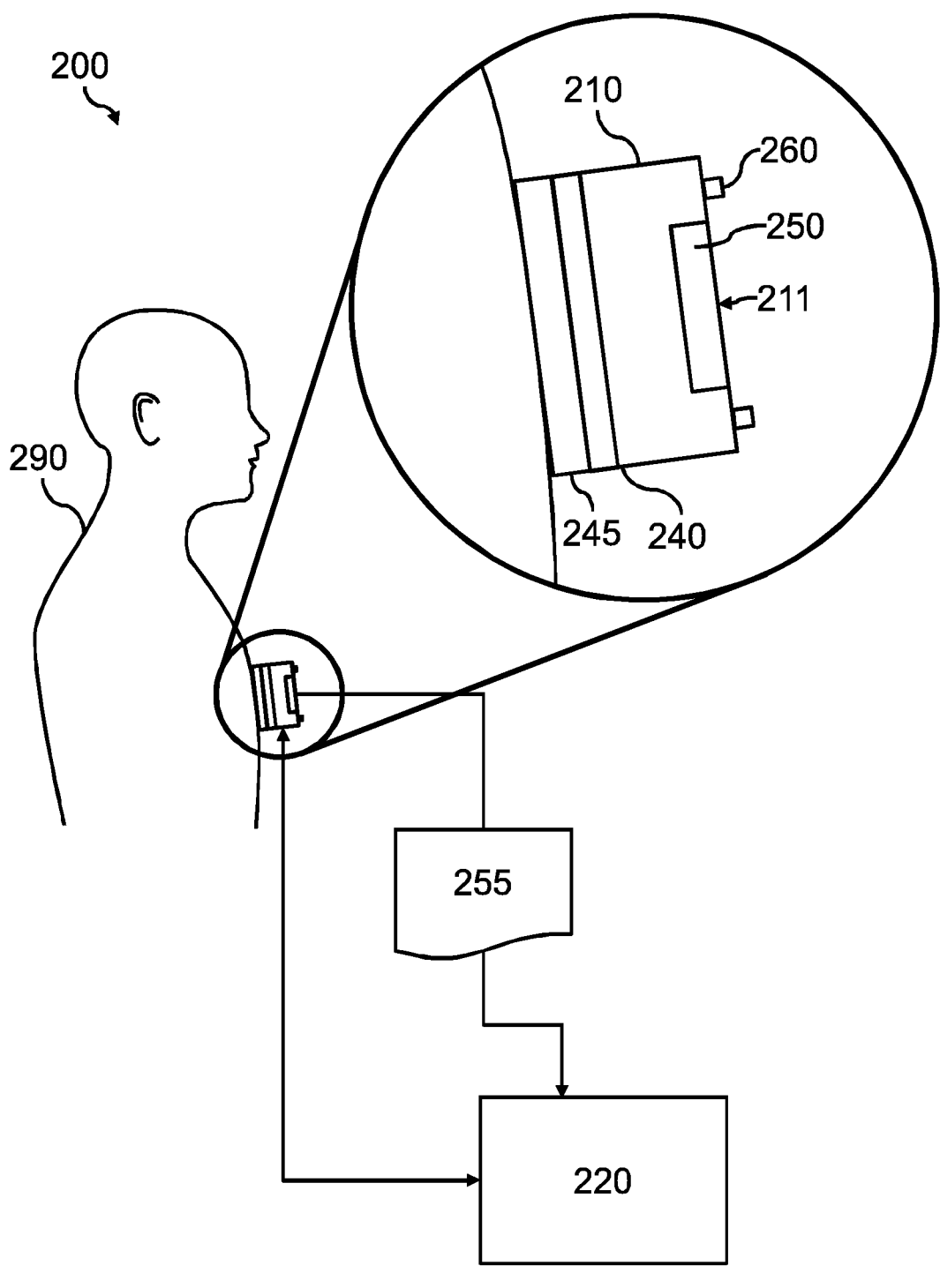
FIG. 2 illustrates an ultrasound system, according to an embodiment of the invention.

FIG. 2 illustrates an ultrasound device 200, according to an embodiment of the invention. The ultrasound device comprises an ultrasound probe 210, and an ultrasound processing system 220 for controlling the ultrasound device.

The ultrasound device 200 may be any suitable ultrasound device. In some examples, the ultrasound device is a wearable ultrasound device, but the invention is not limited to wearable ultrasound devices. An example of a wearable ultrasound probe that may be used as part of the device 200 is described in more detail below.

Although illustrated as a separate component for illustrative clarity, the ultrasound processing system 220 may be formed as part of the ultrasound probe 210, e.g., a processing system formed within the ultrasound probe 210.

The ultrasound device comprises an ultrasound acoustic sensor 240. The ultrasound acoustic sensor 240 is controllable to transmit ultrasound waves and receive echo information, according to well-known ultrasound imaging methodologies such as those previously described. For instance, the ultrasound acoustic sensor may comprise a transducer array 6 for transmitting ultrasound waves and receiving echo information.

In use, an acoustic coupling is formed between the ultrasound acoustic sensor 240 and a subject 290. A high-quality acoustic coupling is required to perform high-quality ultrasound imaging.

The ultrasound device also comprises an actuation mechanism 250. The actuation mechanism is configured to generate an actuation signal 255 that indicates whether or not that there is an interaction between the actuation mechanism 250 and an operator (not shown) of the ultrasound device.

In the embodiment of FIG. 2, the ultrasound acoustic sensor 240 and the actuation mechanism 250 are part of the ultrasound probe 210.

The interaction is one that increases a force applied by the ultrasound device to the subject 290, i.e., increases a force with which the ultrasound acoustic sensor is pressed against the subject. This may be relative to a force applied by the ultrasound device to the subject in the absence of the interaction, e.g., a baseline force.

The ultrasound processing system 220 is configured to initiate ultrasound scanning, i.e., initiate an ultrasound scanning procedure, responsive to the actuation signal indicating that there is an interaction between the actuation mechanism and the operator.

Accordingly, the ultrasound processing system 220 may obtain the actuation signal 255 and process the actuation signal to determine whether or not there is an interaction that increases a force applied by the ultrasound device to the subject, i.e., identify the occurrence or non-occurrence of such an interaction. If such an interaction is detected, then ultrasound scanning is initiated. Otherwise, no ultrasound scanning is initiated.

Figure 3:
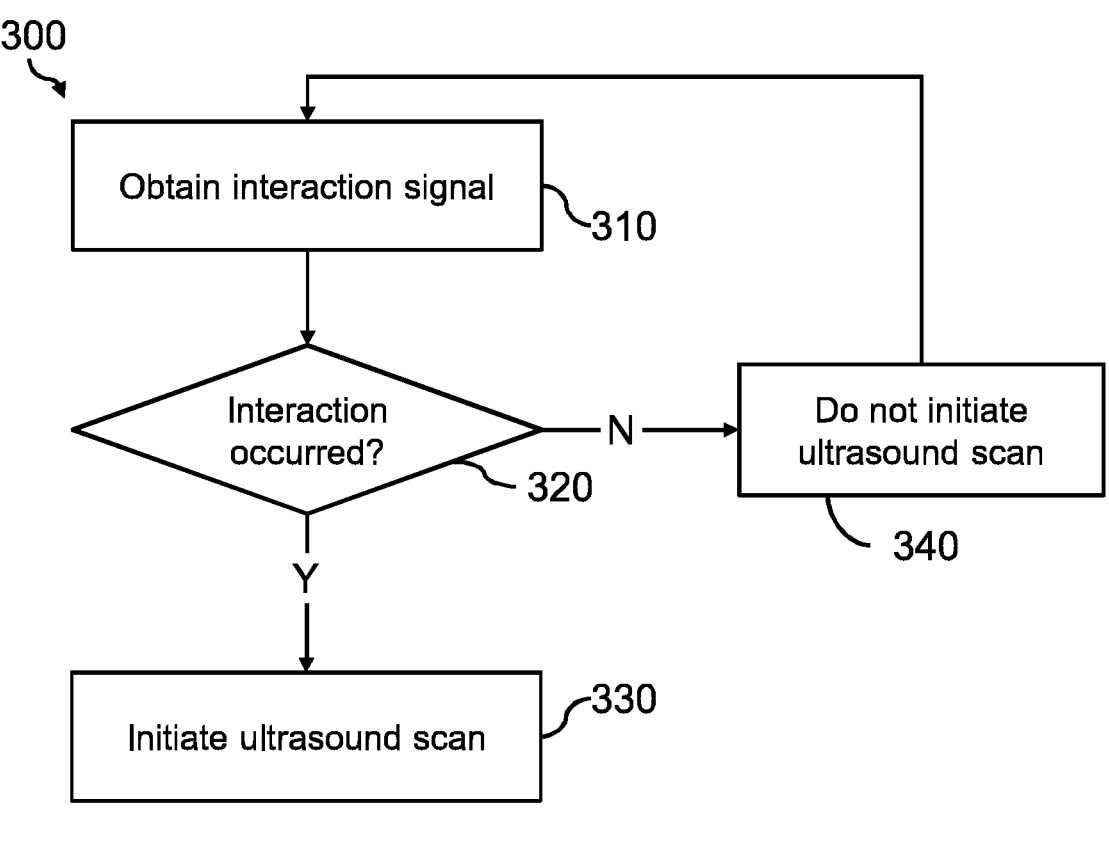
FIG. 3 illustrates a computer-implemented method for controlling an ultrasound device, according to an embodiment of the invention.

For improved contextual understanding, FIG. 3 illustrates a (computer-implemented) method 300 performed by the ultrasound processing system 220. The method 300 is for initiating an ultrasound scan on a subject using an ultrasound device.

The method begins at step 310, which comprises obtaining an actuation signal generated by an actuation mechanism of the ultrasound device. As previously mentioned, the actuation signal indicates whether or not there is an interaction between the actuation mechanism and an operator of the ultrasound device. The interaction is an interaction that increases a force applied by the ultrasound device to a subject.

In determination step 320, the ultrasound processing system processes the interaction signal to determine whether or not an interaction has occurred. Various approaches for performing this step will be later described.

Responsive to determining that an interaction has occurred, the method performs step 330 of initiating ultrasound scanning of the subject, using an ultrasound acoustic sensor of the ultrasound device. Thus, step 330 comprises initiating ultrasound scanning of the subject, using an ultrasound acoustic sensor of the ultrasound device, responsive to the actuation signal indicating that there is an interaction between the actuation mechanism and the operator of the ultrasound device.

Responsive to determining that no interaction has occurred, the method performs step 340 of not initiating ultrasound scanning. Thus, no action to initiate ultrasound scanning is performed. This approach significantly reduces the power consumption of the ultrasound device, as until the ultrasound device is activated, the ultrasound device may consume very little power. The method may then revert back to step 310.

Example approaches for identifying or detecting an interaction that increases the force applied by the ultrasound device to the subject will now be described. Continued reference to FIG. 2 will be made.

In one example, the actuation mechanism 250 comprises a touch sensor. In particular, the touch sensor may be a touch sensor located on a surface of the ultrasound device opposite to an ultrasound-emitting surface of the ultrasound acoustic sensor. The actuation signal generated by the touch sensor may be a signal responsive to a touch at the touch sensor, e.g., a touch at a touch-sensitive surface 211 of the touch sensor. In other words, the actuation signal 255 may carry touch data generated by the touch sensor. Touch sensors are well known in the art. For example, the touch sensor may be a capacitive touch sensor, such as a Cypress CapSense® sensor, or a resistive touch sensor.

Detection of a touch at the touch sensor indicates the occurrence of an interaction that increases a force applied by the ultrasound device to the subject. It has been recognized that touching an appropriately positioned or located touch sensor, such as located on a surface of the ultrasound device opposite to an ultrasound-emitting surface of the ultrasound acoustic sensor, will naturally increase a force applied by the ultrasound device to the subject. In particular, the touch sensor should be placed such that the touch force aligns with a coupling force, being a force that extends from the ultrasound acoustic sensor towards the subject to achieve acoustic coupling for ultrasound imaging.

Accordingly, the ultrasound processing system 220 may be configured to initiate ultrasound scanning of the subject by processing the touch data to determine whether a user is touching the touch sensor. The processing system 220 may initiate ultrasound scanning of the subject responsive to a determination that a user is touching the touch sensor. Thus, a determination that the user is touching the touch sensor may represent a determination that an interaction that increases a force applied by the ultrasound device to the subject has occurred.

In an example, the actuation mechanism 250 may comprise a mechanical button on the surface of the ultrasound device opposite to the ultrasound-emitting surface. The mechanical button may be arranged/positioned so that pushing or pressing the mechanical button increases a force applied by the ultrasound device to the subject.

In this way, detection of whether or not the mechanical button has been activated (e.g., pressed) is a detection as to whether or not an interaction, which increases a force applied by the ultrasound device to a subject, has occurred.

Accordingly, the actuation signal may thereby contain actuation data that indicates whether or not the mechanical button has been pressed.

A simple example of a mechanical button is a mechanical switch. Typically, when a mechanical switch is activated by an operator, the switch closes and causes current to flow. This current flow can, for instance, pull an actuation signal high, e.g., connect a node providing the actuation signal to a high voltage, or pull the actuation signal low, e.g., connect a node providing the actuation signal to a low or ground voltage.

The ultrasound processing system 220 may be configured to initiate ultrasound scanning of the subject by processing the actuation data to determine whether a user is pressing the mechanical button. The processing system 220 may initiate ultrasound scanning of the subject responsive to a determination that the mechanical button has been pushed or pressed. Thus, a determination that the user is has pressed/pushed the mechanical button may represent a determination that an interaction that increases a force applied by the ultrasound device to the subject has occurred.

In an example, the actuation mechanism 250 may comprise a pressure sensor. The pressure sensor may be part of the ultrasound probe, or may be a separate device positioned between the ultrasound probe and the subject.

The pressure sensor detects a pressure exerted by the ultrasound device 200 on the subject or the pressure exerted by an operator on the ultrasound device (in a direction of the subject). Examples of suitable pressure sensors, including MEMS pressure sensors, will be apparent to the skilled person. The pressure sensor may generate pressure data responsive to the detected pressure. For the avoidance of doubt, it is noted that such a pressure sensor determines a pressure or generates pressure data without the use of ultrasound.

Alternative labels for a pressure sensor include: pressure transducer; force sensor; force transducer; strain transducer; or a strain sensor. In the context of the present disclosure, the pressure sensor will generate pressure data that changes responsive to changes in a pressure and/or force being applied to the pressure sensor. Examples include force-sensing resistors, capacitive/inductive/piezoelectric load cells; strain gauges and so on.

The ultrasound processing system may be configured to process the pressure to determine whether the pressure exceeds an activation pressure threshold. This can be performed, for instance, by processing the pressure data to identify or calculate a pressure exerted by the ultrasound device on the subject, and comparing this calculated pressure to the activation pressure threshold. Calculating a pressure comprises calculating a value of the pressure.

The ultrasound processing system 220 may be configured to initiate ultrasound scanning responsive to determining that the pressure exceeds the activation pressure threshold. Otherwise, no ultrasound scanning may be initiated or performed.

The above-described embodiments provide approaches for initiating an ultrasound scanning procedure responsive to detecting an interaction.

Initiating the ultrasound scanning procedure comprises initiating an initial frame rate scan of the subject at an initial frame rate. Ultrasound data generated at this initial frame rate is processed (by the ultrasound processing system 220) to identify a pressure exerted or applied by the ultrasound device on the subject. Thus, ultrasound data generated during the initial frame rate scan (at the initial frame rate) is processed to identify pressure data, i.e., ultrasound-derived pressure data.

For instance, the pressure may be determined by processing the ultrasound imaging data to determine a compression of the subject's tissue (e.g. skin tissue). A detailed exemplary approach for determining a pressure from ultrasound data is described in U.S. Pat. No. 8,753,278 (Stoll).

A pressure may also be determined from ultrasound data by making use of an acoustically translucent standoff 245, positioned between a surface of the ultrasound probe 210 and the subject 290. This acoustically translucent standoff 245 may form part of the ultrasound device 200. The acoustically translucent standoff is a layer of material that has an acoustic transparency that allows ultrasound imaging through the material (e.g., the acoustically translucent standoff may be an aqueous gel pad). The processing system 220 determines the pressure exerted by the ultrasound device on the subject by processing the ultrasound imaging data to determine a measure of deformation (e.g., an axial strain) of the acoustically translucent standoff.

In some examples, the processing system may determine the measure of deformation based on a depth of a distal surface of the acoustically translucent standoff 245 (i.e., a surface furthest from the ultrasound probe 210). In other words, the measure of deformation may be determined based on a depth of a boundary between the acoustically translucent standoff and a layer on the opposite side of the acoustically translucent standoff to the ultrasound device (e.g., the subject's skin).

The processing system may determine the measure of deformation based on distal surface depth by: identifying a plurality of ultrasound echoes from each of one or more scan lines in the ultrasound imaging data; processing, for each scan line, the plurality of echoes from the scan line to determine a depth of a distal surface of the acoustically translucent standoff; and processing the depth of the distal surface for each of the one or more scan lines to determine the measure of deformation.

The depth of the distal surface for a particular scan line may be determined by processing the plurality of echoes from the scan line to identify an echo for which a signal intensity value first exceeds an intensity threshold. Since an adjacent layer to the distal surface (e.g., skin, adhesive, air, etc.) will generally have a different acoustic impedance to the acoustically translucent standoff, the boundary between the acoustically translucent standoff and an adjacent layer will be characterized by an upward transition in signal intensity.

The plurality of echoes may be processed in order of increasing depth; the first echo to be identified as having a signal intensity value exceeding the intensity threshold is then selected as the echo corresponding to the distal surface for the scan line. The depth of the identified echo is selected as the depth of the distal surface for the scan line. This process is repeated for each scan line.

The intensity threshold may be a predetermined threshold determined based on the characteristics of both the ultrasound probe 210 and the acoustically translucent standoff 245. These characteristics may be obtained via user input and/or stored in a memory unit (not shown in FIG. 2). In some examples, a plurality of predetermined intensity thresholds, each for a different combination of ultrasound device and acoustically translucent standoff may be stored in the memory unit, and a suitable predetermined intensity threshold may be selected based on user input from a user input device.

The processing system may also/alternatively determine a value for the intensity threshold by processing the ultrasound signal. The processing system may determine the intensity threshold based on signal intensity values of the ultrasound signal (e.g., based on an average minimum signal intensity and an average maximum signal intensity). For instance, the intensity threshold may be set at a value between the average minimum signal intensity and the average maximum signal intensity (e.g., at a midpoint between these signal intensities, or a value between the midpoint and the average maximum signal intensity).

The ultrasound imaging data may be preprocessed before determining the distal surface depth(s). For example, automatic time gain compensation (TGC) may be used to auto-normalize the brightness across a scan line.

The depth of the distal surface corresponds to a current thickness of the acoustically translucent standoff 245. The distal surface depths may be used in conjunction with one or more characteristics of the acoustically translucent standoff to determine the deformation of the acoustically translucent standoff. The one or more characteristics may comprise at least one of: a thickness in a zero-force state, a thickness at a predefined non-zero compression force or pressure, and/or an elastic modulus. These characteristics may be obtained via user input and/or stored in a memory unit.

In some examples, where a large number of scan lines are used, the determined distal surface depths may be preprocessed before determining the measure of deformation. For instance, an outlier analysis may be applied to the determined distal surface depths in order to identify false positives, which may be excluded from the distal surface depths used to determine the measure of deformation.

The depth of the distal surface may be averaged across multiple scan lines before determining the measure of deformation; the number of scan lines over which the depth of the distal surface is averaged may depend on a desired level of granularity. In some examples, the number of scan lines over which the depth of the distal surface is averaged may be selected to produce one average depth per frame (e.g., the distal surface depth may be averaged across approximately 128 scan lines).

In examples, the processing system may determine the measure of deformation based on cross-correlation with a reference image. The reference image is an image that corresponds to an ultrasound image of the acoustically translucent standoff 245 when no force is deforming the acoustically translucent standoff (e.g., an image taken in air).

Cross-correlation is a well-known technique in the field of image processing, and can be used to measure a displacement of a structure between two images. See, for example, Bilgen and Insana (1996), "Deformation models and correlation analysis in elastography", J. Accoust. Soc. Am., 99(5):3212-3224; and Pinton et al. (2006), "Rapid tracking of small displacements using ultrasound", IEEE Transactions on Ultrasonics, Ferroelectrics, and Frequency Control, 53(6):1103-1117.

By cross-correlating an ultrasound image of the deformed acoustically translucent standoff 245 with an ultrasound image of the non-deformed acoustically translucent standoff (i.e., when no force is applied), the displacement in the direction of the imaging axis (i.e. the axial strain) may be determined. The cross-correlation may be a series of 1D azimuthal line correlations or a 2D cross-correlation.

In some examples, the reference image may be obtained by a user of the ultrasound system imaging the acoustically translucent standoff 245. The user may be prompted to take this image, e.g., by outputting a user instruction to a user interface.

In examples, the reference image may be generated from the ultrasound imaging data. The processing system may process the ultrasound imaging data to generate a plurality of frames, and the first frame having image contents (i.e., the first frame that is not entirely black) may be selected as the reference image, while a later frame may be selected as the ultrasound image that is cross-correlated with the reference image.

In examples, the reference image may be a simulated image, generated from data representative of the acoustically translucent standoff when no force is applied.

The generated image (and/or the reference image) may be preprocessed before the cross-correlation is performed. Parameters used in the preprocessing may be selected based on the imaging frequency used by the ultrasound probe 210 when acquiring the ultrasound imaging data and one or more characteristics of the acoustically translucent standoff. Suitable image processing techniques for preprocessing the generated image, such as axial interpolation and azimuthal decimation, will be apparent to the skilled person.

The measure of deformation may be determined based on the results of the cross-correlation. For instance, the measure of deformation may be an axial strain, determined as the displacement in the direction of the imaging axis based on the cross-correlation.

The processing system 220 may determine the pressure exerted by the ultrasound device 200 by processing the determined measure of deformation and one or more characteristics of the acoustically translucent standoff 245 (e.g., a thickness in a zero-force state, a thickness at a predefined non-zero compression force or pressure, and/or an elastic modulus). The relationships between force/pressure and axial strain (or a deformed thickness) are very well known, so methods for determining a pressure exerted by the ultrasound device based on a measure of deformation and one or more characteristics of the acoustically translucent standoff will be readily apparent to the skilled person. In some examples, the determination may be further based on a surface area of the ultrasound emitting surface of the ultrasound acoustic sensor (i.e., the surface in contact with or closest to the acoustically translucent standoff layer). The one or more characteristics and/or the surface area may, for example, be obtained via user input or stored in a memory unit.

When an initial frame rate scan of the subject (at an initial frame rate) to determine pressure data takes place, ultrasound scanning of the subject at a desired frame rate (a "full frame rate scan" or "desired frame rate scan") responsive to a determination that the pressure exceeds a full scan pressure threshold is initiated, wherein the desired frame rate is higher than the initial frame rate.

The desired frame rate may be greater than 10 frames per second, e.g., greater than 20 frames per second. For instance, the desired frame rate may be between 10 and 30 frames per second. The skilled person will appreciate that the frame rate may be bounded or restricted by the precise ultrasound acoustic sensor in use, the capabilities of the ultrasound device and/or the characteristics of the ultrasound scan (e.g., the line density and/or sector width, as well as the depth of the deepest image signal that is processed).

The initial frame rate is lower than the desired frame rate, e.g., less than 10 frames per second.

In this way, the processing system 220 may (when an interaction is determined without the use of a pressure sensor) control the ultrasound device 200 to acquire ultrasound imaging data at a lower frame rate until it is determined that the pressure exceeds the full scan pressure threshold. This approach allows ultrasound imaging data to be used to determine the pressure exerted by the ultrasound device, while consuming less power than is required for full frame rate scanning (i.e., scanning at the desired frame rate).

Thus, scanning at the lower/initial frame rate may be activated by a non-pressure detecting actuation mechanism (e.g., the use of a touch sensor or mechanical button). The ultrasound imaging device may acquire no ultrasound imaging data until the lower/initial frame rate scan is activated. This again enables low power consumption of the ultrasound device between scans. In other words, an initial (low) frame rate scan may be activated in response to a user touching the ultrasound device 200, and a full frame rate ultrasound scan is activated once the initial frame rate ultrasound imaging data indicates that the user is pressing with sufficient pressure to exceed the full scan pressure threshold.

In examples in which the actuation mechanism is a pressure sensor, then initiating ultrasound scanning may comprise initiating the ultrasound scanning at the desired frame rate (i.e., perform the full frame rate scan) when the determined pressure exceeds an activation pressure threshold. Thus, if a pressure sensor is used, ultrasound scanning at the initial/lower frame rate can be skipped/omitted.

The full scan pressure threshold (for use when an initial frame rate scan is performed) or the activation pressure threshold (for use when a pressure sensor detects a pressure) may be a predetermined (e.g., non-zero) pressure threshold for providing a desired coupling pressure, and may depend on an ultrasound imaging application. For instance, the threshold may have a higher value for cardiac and lung imaging than for vessel imaging at the neck, as greater pressure is required in cardiac and lung imaging in order to obtain clinically useful results.

In examples in which the actuation mechanism does not comprise a pressure sensor, although preferred, it is not essential to perform the initial frame rate scan. Rather, detection of the interaction (e.g., a touch at a touch sensor or push or a mechanical button) may simply initiate the full frame rate scan.

In some examples, the processing system 220 is further configured to provide feedback to a user of the ultrasound device 200, by controlling a feedback unit to provide a user-perceptible output. In FIG. 2, the feedback unit is a plurality of LEDs 260 positioned at or near the perimeter of the ultrasound device. This positioning allows light emitted by at least one of the LEDs to be seen by the user even when most of the ultrasound device is covered by the user's hand. However, the feedback unit is not limited to LEDs: the feedback unit may be or comprise any device suitable for providing a user-perceptible output (e.g., a haptic, audio and/or visual indicator), such as a display device, a speaker, a light, or a vibrator. The user-perceptible output may comprise, for example, one or more of: an image, a light, a textual display, a sound and/or a vibration.

Feedback provided to the user may comprise one or more of: an indication that more pressure is required, an indication that a current pressure is correct, an indication that scanning is completed, an indication that it is time to perform a scan, an indication that data is being transferred from the ultrasound device to the processing system and/or an indication that the battery of the ultrasound device is low. Such feedback may be used to guide a user with little or no sonography experience to perform an ultrasound scan that is likely to result in clinically useful imaging data.

In examples in which the feedback unit 260 is used to provide a plurality of user-perceptible outputs (each representative of a different indication), the processing system 220 may control the feedback unit to provide different user-perceptible outputs for different indications. For instance, where the feedback unit comprises one or more LEDs (as in FIG. 2), different LEDs (i.e., in different positions), or different color lights and/or flashing/non-flashing lights may be used to provide different indications (e.g., a yellow light to indicate that more pressure is required, a flashing green light to indicate that a current pressure is correct and a scan is in progress, a solid—i.e., non-flashing—green light to indicate that scanning is completed, a blue light to indicate the transfer of data, and a red light to indicate low battery). Methods for providing different user-perceptible outputs for other types of feedback unit will be apparent to the skilled person (e.g., vibration signals having different intensities, patterns and/or durations for a feedback unit comprising a vibrator).

In particular, the processing system 220 may, for example, generate an indication that more pressure is required in response to a determination that a pressure does not exceed the full scan pressure threshold (when an initial frame rate scan is performed) or the activation pressure threshold (when a pressure sensor detects a pressure). The processing system may control the feedback unit 260 to provide a user-perceptible output representative of the indication that more pressure is required.

Thus, in any embodiment in which pressure data is obtained (either by processing ultrasound data or directly from a pressure sensor), feedback can be provided that indicates whether a determined pressure has reached a pressure threshold for performing a ultrasound imaging scan at a desired frame rate.

In examples, the processing system 220 may generate the indication that more pressure is required only when the processing system determines that the ultrasound device 200 is in use (i.e., that a user is attempting to activate an ultrasound scan), but that a determined pressure does not exceed the full scan pressure threshold (when an initial frame rate scan is performed) or the activation pressure threshold (when a pressure sensor detects a pressure).

For instance, where the actuation mechanism comprises a touch sensor, the processing system 220 may generate the indication that more pressure is required in response to a determination that the pressure (derived from ultrasound data) does not exceed the full scan pressure threshold and a determination that a user is touching the touch sensor of the ultrasound device.

Where the actuation mechanism comprises a pressure sensor, the processing system may generate the indication that more pressure is required in response to a determination that the pressure (derived from the pressure data produced by the pressure sensor) does not exceed the activation pressure threshold, but does exceed an interaction pressure threshold (which is lower than the activation pressure threshold). The interaction threshold may be a non-zero pressure threshold, to reduce the effect of indications generated due to noise.

In some examples, the processing system 220 may generate an indication that a current pressure is correct in response to a determination that the pressure exceeds the full scan pressure threshold (when an initial frame rate scan is performed) or the activation pressure threshold (when a pressure sensor detects a pressure). This may be in addition to, or performed concurrently with, controlling the ultrasound device 200 to acquire ultrasound imaging data at the desired frame rate. Thus, when ultrasound scanning at the desired frame rate is performed, the processing system may simultaneously control the feedback unit 260 to provide a user-perceptible output representative of the indication that the current pressure is correct.

In some examples, the processing system 220 may generate an indication that scanning is completed in response to a determination that the ultrasound device 200 has obtained a desired amount of ultrasound imaging data, and control the feedback unit 260 to provide a user-perceptible output representative of the indication that scanning is completed.

The processing system 220 may determine whether the ultrasound device 200 has obtained a desired amount of ultrasound imaging data during an ultrasound scan based on scanning time and/or the ultrasound imaging data acquired during the scan (i.e., the ultrasound imaging data acquired at the desired frame rate). How the processing system determines whether the ultrasound device has obtained a desired amount of ultrasound imaging data may depend on an imaging application. For instance, for more straightforward types of ultrasound procedures, a scanning time may be sufficient to determine whether a desired amount of ultrasound imaging data has been obtained (e.g., the processing system may determine that the ultrasound device has obtained a desired amount of ultrasound imaging data in response to a scanning time exceeding a predetermined scanning time threshold). For example, in the case of cardiac ultrasound, a scanning time of six seconds may be considered sufficient to capture ultrasound imaging data over at least three cardiac beat cycles.

In some examples, the processing system 220 may determine whether a desired amount of ultrasound imaging data has been obtained based on acquired ultrasound imaging data by applying heuristic checks. Suitable heuristic checks will be apparent to the skilled person. For example, standard heuristic checks on ultrasound imaging data used to detect sufficient coupling may be used in combination with a scanning time. In other words, the processing system may determine that the ultrasound device 200 has obtained a desired amount of ultrasound imaging data in response to a heuristic check indicating that the ultrasound device is sufficiently coupled to the subject and a scanning time exceeding a predetermined scanning time threshold.

In examples, the processing system 220 may determine whether a desired amount of ultrasound imaging data has been obtained based on acquired ultrasound imaging data using one or more machine-learning algorithms. Machine-learning techniques for analyzing ultrasound imaging data are very well-known, and suitable machine-learning algorithms for determining whether a desired amount of ultrasound data has been obtained will be apparent to the skilled person. For example, the processing system 220 may process the acquired ultrasound imaging data using a machine-learning algorithm trained to identify one or more anatomical structures in the ultrasound imaging data, and determine that the ultrasound device has obtained a desired amount of ultrasound imaging data in response to one or more predefined anatomical structures have been identified.

In some examples, the processing system 220 may control the ultrasound device 200 to stop acquiring ultrasound imaging data at the desired frame rate in response to a determination that the ultrasound device has obtained a desired amount of ultrasound imaging data.

In some examples, the processing system 220 may end the ultrasound scan when the user stops pressing the ultrasound device against the subject (i.e., the processing system may control the ultrasound device to stop acquiring ultrasound imaging data at the desired frame rate in response to a determination that the interaction has ended).

The user may stop pressing on the ultrasound device in response to an indication that scanning is completed, or decide when to stop the scan based on their own judgment (e.g., where no indication is provided, or in spite of an indication, in order to obtain additional ultrasound imaging data to increase a likelihood of accurate diagnosis).

In some examples, the processing system 220 may generate an indication that it is time to perform a scan in response to a determination that a time since the ultrasound device 200 most recently acquired ultrasound imaging data (i.e., a time since the last scan) exceeds a predetermined period. The predetermined period will depend on a scanning application, and may be determined according to clinical guidelines. For instance, the predetermined period may be a predetermined number of hours or days (e.g. an ultrasound scan may be performed once a day). The processing system may then control the feedback unit 260 to provide a user-perceptible output representative of the indication that it is time to perform a scan.

Figure 4:
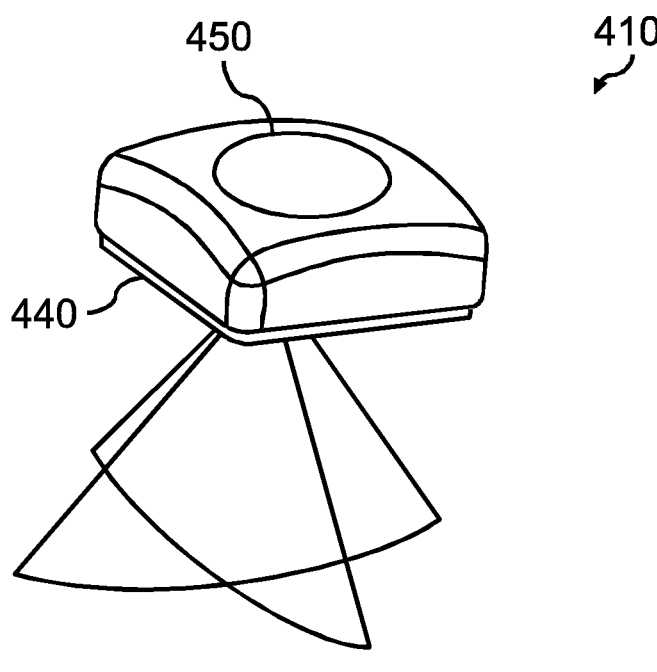
FIG. 4 illustrates a wearable ultrasound device that may be used in the system of FIG. 2.

FIG. 4 illustrates a wearable ultrasound probe 410 that may be used with the device 200 described above. The wearable ultrasound probe is a small, reusable, wireless ultrasound scanner capable of 2D and/or 3D imaging. The wearable ultrasound probe may, for example, comprise a matrix sensor.

The wearable ultrasound probe 410 may comprise an integrated signal path, battery, BLE radio and microcontroller, and may further comprise an ultrasound processing system configured to initiate ultrasound scanning as described above. The wearable ultrasound probe may additionally or alternatively communicate wirelessly with a separate processing system that receives and processes ultrasound imaging data acquired by the wearable ultrasound probe at the desired frame rate. The battery may be rechargeable.

An acoustically translucent standoff 440 may be attached to an ultrasound-emitting surface of the wearable ultrasound probe 410. When the wearable ultrasound probe is in use, the acoustically translucent standoff is therefore between the probe and a subject, and the pressure exerted by the wearable ultrasound probe and the subject may be determined by processing acquired ultrasound imaging data to determine a measure of deformation of the acoustically translucent standoff. The acoustically translucent standoff 440 may comprise an adhesive layer on the surface on the opposite side of the acoustically translucent standoff to the wearable ultrasound probe 410, for attaching the acoustically translucent standoff (and therefore the wearable ultrasound probe) to a subject. In examples without an acoustically translucent standoff, the ultrasound probe may comprise an adhesive layer for attaching the ultrasound probe to the subject). In some examples, the adhesive layer may be disposed only around the perimeter of the surface of the acoustically translucent standoff or ultrasound probe, with a window in the adhesive layer through which an ultrasound signal may be emitted.

The use of an adhesive layer allows the wearable ultrasound probe 410 to remain attached to the body between ultrasound scans. This ensures a consistent position of the wearable ultrasound probe between ultrasound scans, enabling more accurate longitudinal measurement repetitions, and reduces the number of times that the wearable ultrasound probe needs to be sterilized (only when it is removed from the subject). It also allows a particular wearable ultrasound probe to be associated with a particular subject in terms of subject data generation. In examples, the ultrasound probe may be a pocketable probe, which is held against the subject by a user (who may or may not be the subject) during ultrasound scans.

An actuation mechanism 450 is provided on the wearable ultrasound probe 410, preferably on the surface opposite to the ultrasound-emitting surface.

The actuation mechanism may, for instance, comprise a touch button that detects a touch of a user. An initial frame rate scan may be activated in response to the touch button detecting a touch, as described above. Ultrasound imaging data acquired at the initial frame rate can be processed to determine the pressure exerted by the wearable ultrasound probe on the subject, and the ultrasound wearable probe can be controlled to acquire ultrasound imaging data at the desired frame rate in response to a determination that the pressure exceeds the full scan pressure threshold.

A feedback unit may be integrated into the actuation mechanism 450. For instance, the actuation mechanism may comprise an integrated light indicator, and light up to provide an indication to a user (e.g. that more pressure is required). The actuation mechanism may glow in different colors to provide different indications.

In some examples, the ultrasound device is dormant (not emitting/receiving ultrasound) when no interaction takes place. Accordingly, in some examples, any ultrasound scanning procedure is terminated if the interaction ends, i.e., the increased force is removed or reduced.

It will be understood that the disclosed methods are computer-implemented methods. As such, there is also proposed a concept of a computer program comprising code for implementing any described method when said program is run on a processing system.

The skilled person would be readily capable of developing a processor for carrying out any herein described method. Thus, each step of a flow chart may represent a different action performed by a processor, and may be performed by a respective module of the processor.

As discussed above, the system makes use of a processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

Functions implemented by a processor may be implemented by a single processor or by multiple separate processing units which may together be considered to constitute a "processor". Such processing units may in some cases be remote from each other and communicate with each other in a wired or wireless manner.

Measures recited in mutually different dependent claims may advantageously be combined.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. An ultrasound device for scanning a subject, the ultrasound device comprising:
   an ultrasound acoustic sensor;
   an actuation mechanism configured to generate an actuation signal that indicates whether or not there is an interaction between the actuation mechanism and an operator of the ultrasound device, wherein the interaction increases a force applied by the ultrasound device to the subject; and
   an ultrasound processing system configured to
      initiate ultrasound scanning of the subject at an initial frame rate, using the ultrasound acoustic sensor, responsive to the actuation signal indicating that there is the interaction between the actuation mechanism and the operator of the ultrasound device;
      obtain ultrasound imaging data acquired by the ultrasound acoustic sensor at the initial frame rate;
      process the ultrasound imaging data to determine a pressure exerted by the ultrasound device on the subject; and
      initiate ultrasound scanning of the subject at a second frame rate responsive to a determination that the pressure exceeds a full scan pressure threshold, wherein the second frame rate is greater than the initial frame rate.

2. The ultrasound device of claim 1, wherein:
   the actuation mechanism comprises a touch sensor located on a surface of the ultrasound device opposite to an ultrasound-emitting surface of the ultrasound acoustic sensor;
   the actuation signal carries touch data from the touch sensor; and
   the ultrasound processing system initiates ultrasound scanning of the subject by:
      processing the touch data to determine whether a user is touching the touch sensor; and
      initiating ultrasound scanning of the subject responsive to a determination that the user is touching the touch sensor.

3. The ultrasound device of claim 1, wherein the ultrasound processing system is further configured to, in response to a determination that the pressure does not exceed the full scan pressure threshold:
   generate an indication that more pressure is required; and
   control a feedback unit to provide a user-perceptible output representative of the indication that more pressure is required.

4. The ultrasound device of claim 1, wherein the ultrasound processing system is further configured to, in response to a determination that the pressure exceeds the full scan pressure threshold:
   generate an indication that a current pressure is correct; and
   control the feedback unit to provide a user-perceptible output representative of the indication that the current pressure is correct.

5. The ultrasound device of claim 1, wherein the ultrasound processing system is further configured to control the ultrasound device to stop ultrasound scanning of the subject in response to a determination that the pressure no longer exceeds the full scan pressure threshold.

6. The ultrasound device of claim 1, wherein:

the actuation mechanism comprises a pressure sensor;

the actuation signal carries pressure data from the pressure sensor; and the ultrasound processing system initiates ultrasound scanning of the subject by:

processing the pressure data to determine the pressure exerted by the ultrasound device on the subject; and initiating ultrasound scanning of the subject responsive to a determination that the pressure exceeds an activation pressure threshold.

7. The ultrasound device of claim 6, wherein the ultrasound processing system is further configured to, in response to a determination that the pressure does not exceed the activation pressure threshold but does exceed an interaction pressure threshold that is lower than the activation pressure threshold:

generate an indication that more pressure is required; and control the feedback unit to provide a user-perceptible output representative of the indication that more pressure is required.

8. The ultrasound device of claim 1, wherein the ultrasound processing system is further configured to:

determine whether the ultrasound device has obtained a desired amount of ultrasound imaging data during a current ultrasound scan;

generate an indication that scanning is completed in response to a determination that the ultrasound device has obtained the desired amount of ultrasound imaging data; and control the feedback unit to provide a user-perceptible output representative of the indication that scanning is completed.

9. The ultrasound device of claim 1, wherein the ultrasound processing system is further configured to:

determine a time since the ultrasound device most recently acquired ultrasound imaging data;

and, in response to a determination that the time since the ultrasound device most recently acquired ultrasound imaging data exceeds a predetermined period:

generate an indication that it is time to perform a scan; and control the feedback unit to provide a user-perceptible output representative of the indication that it is time to perform a scan.

10. The ultrasound device of claim 1, wherein the ultrasound device comprises an adhesive layer for attaching the ultrasound device to the subject.

11. The ultrasound device of claim 10, wherein the ultrasound device further comprises an acoustically translucent standoff on an opposite surface of the adhesive layer to a surface for attaching the ultrasound device to the subject.

12. The ultrasound device of claim 1, wherein the ultrasound device further comprises a feedback unit comprising one or more LEDs positioned at or near a perimeter of the ultrasound device and controllable by the ultrasound processing system.

13. A computer-implemented method for initiating an ultrasound scan on a subject using an ultrasound probe, the computer-implemented method comprising:

obtaining an actuation signal generated by an actuation mechanism of the ultrasound probe, wherein the actuation signal indicates whether or not there is an interaction between the actuation mechanism and an operator of the ultrasound probe, wherein the interaction increases a force applied by the ultrasound device to the subject; and initiating ultrasound scanning of the subject at an initial frame rate, using an ultrasound acoustic sensor of the ultrasound probe, responsive to the actuation signal indicating that there is the interaction between the actuation mechanism and the operator of the ultrasound probe;

obtaining ultrasound imaging data acquired by the ultrasound acoustic sensor at the initial frame rate;

processing the ultrasound imaging data to determine a pressure exerted by the ultrasound probe on the subject; and initiating ultrasound scanning of the subject at a second frame rate responsive to a determination that the pressure exceeds a full scan pressure threshold, wherein the second frame rate is greater than the initial frame rate.

14. A computer program product comprising code which, when executed on a computer device having an ultrasound processing system, causes the ultrasound processing system to perform the method according to claim 13.

15. An ultrasound processing system configured to perform the method according to claim 13.

\* \* \* \* \*